United States Patent [19]

Sprague

[11] 4,430,078
[45] Feb. 7, 1984

[54] BLOOD INFUSION PUMP

[76] Inventor: Leland L. Sprague, 1810 Marisol Dr., Ventura, Calif. 93001

[21] Appl. No.: 257,325

[22] Filed: Apr. 24, 1981

[51] Int. Cl.³ .............................................. A61M 5/00
[52] U.S. Cl. ........................... 604/141; 128/DIG. 12; 222/94; 222/95; 604/118
[58] Field of Search ....... 128/214 F, 214 E, DIG. 12; 222/94–96, 105; 604/140–141, 118

[56] References Cited

U.S. PATENT DOCUMENTS

| | | | |
|---|---|---|---|
| 3,640,276 | 2/1972 | Dancy | 128/214 F |
| 3,640,277 | 2/1972 | Adelberg | 128/214 F |
| 3,895,741 | 7/1975 | Nugent | 128/214 F |

Primary Examiner—Dalton L. Truluck
Attorney, Agent, or Firm—Jack C. Munro

[57] ABSTRACT

A blood infusion pump designed to be employed in combination with a blood bag. The blood bag is located within a storage container. The storage container includes an inflatable bladder. Pressurized fluid is to be conducted within the inflatable bladder which presses against the blood bag to cause dicharge of the blood from the blood bag through a discharge conduit assembly. The container which contains a supply of pressurized fluid is mounted within the housing of the pump of this invention and is connected to the inflatable bladder. There is an access door into the storage chamber, which when opened, prevents the conducting of pressurized fluid to the inflatable bladder through a valve assembly and the simultaneous venting of the inflatable bladder to the ambient.

9 Claims, 6 Drawing Figures

BLOOD INFUSION PUMP

BACKGROUND OF THE INVENTION

The field of this invention relates to a pump, and more particularly to a blood infusion pump which is designed to be employed in combination with a blood bag for the purpose of causing a metered discharge of blood.

It is common knowledge that when a transfusion is being given to a human being, it is necessary to locate the supply of blood a distance above the transfusion area so that gravity will cause the blood to be forced into the patient. This is a conventional blood infusion process. The primary disadvantage to this type of process is that there is no way to increase the flow of blood into the patient, as it is controlled by the force of gravity.

In recent years, hospitals have employed blood infusion pumps. Most blood infusion pumps are designed to be employed in combination with a blood bag. A blood bag is the conventional way in which blood is stored and then utilized. One common type of a blood infusion pump takes the form of a spring biased plate which is to press against the blood bag, and will thereupon create the sufficient pressure to push the blood out of the blood bag and into the patient. One problem with such a spring biased plate is that as the blood bag empties, the pressure diminishes. This lack of constant pressure inherently causes a variance of the rate of flow of blood into the patient. It is most desirable to have the rate of flow be constant so that the precise quantity of blood that is being given to the patient in a set period of time can be known. Also, blood can be given to a patient at a known maximum rate which can maximize the blood intake by the patient, which may be very desirable at certain times.

Additionally, other conventional blood infusion pumps are driven by electricity. However, if an electrical power outage occurs, the electrically operated blood infusion pump no longer is operable. At certain times, this could very create an extremely critical situation.

There is a need for a blood infusion pump which is operated in a manner to discharge blood at a precisely controlled, constant rate. Also, there is a need for a blood infusion pump wherein the rate of discharge of blood can be readily varied. Further, there is a need for a blood infusion pump which is operated independently of outside sources of energy.

SUMMARY OF THE INVENTION

The blood infusion pump of this invention takes the form of a housing which includes a transparent access door. The access door provides access into a blood bag storage chamber. The access door is normally closed around the blood bag during operation of the blood infusion pump. Also located within the storage chamber is an inflatable bladder which is of a size approximately equal to the exterior area of the blood bag. The inflatable bladder is to be supplied a pressurized fluid (gas) to apply pressure against the blood bag. The pressurized fluid is derived from a pressurized container. The pressurized fluid container is mounted within the housing of the pump. The housing includes a support for the container with the support being adjustable to compensate for different heights of pressurized containers. A leak proof sealing arrangement is connectable with the fluid outlet valve of the pressurized container. A pressure relief valve assembly is included which terminates the supply of pressurized fluid to the inflatable bladder upon opening of the access door. Also, at the same time, the inflatable bladder is vented to the ambient. The housing includes a pressure regulator so as to permit variance of the pressure applied against the blood bag. Also, a readable pressure gauge is provided. A separate on-off valve is also provided for the supply of the pressurized fluid to the inflatable bladder.

DETAILED DESCRIPTION OF THE SHOWN EMBODIMENT

Figure 1:
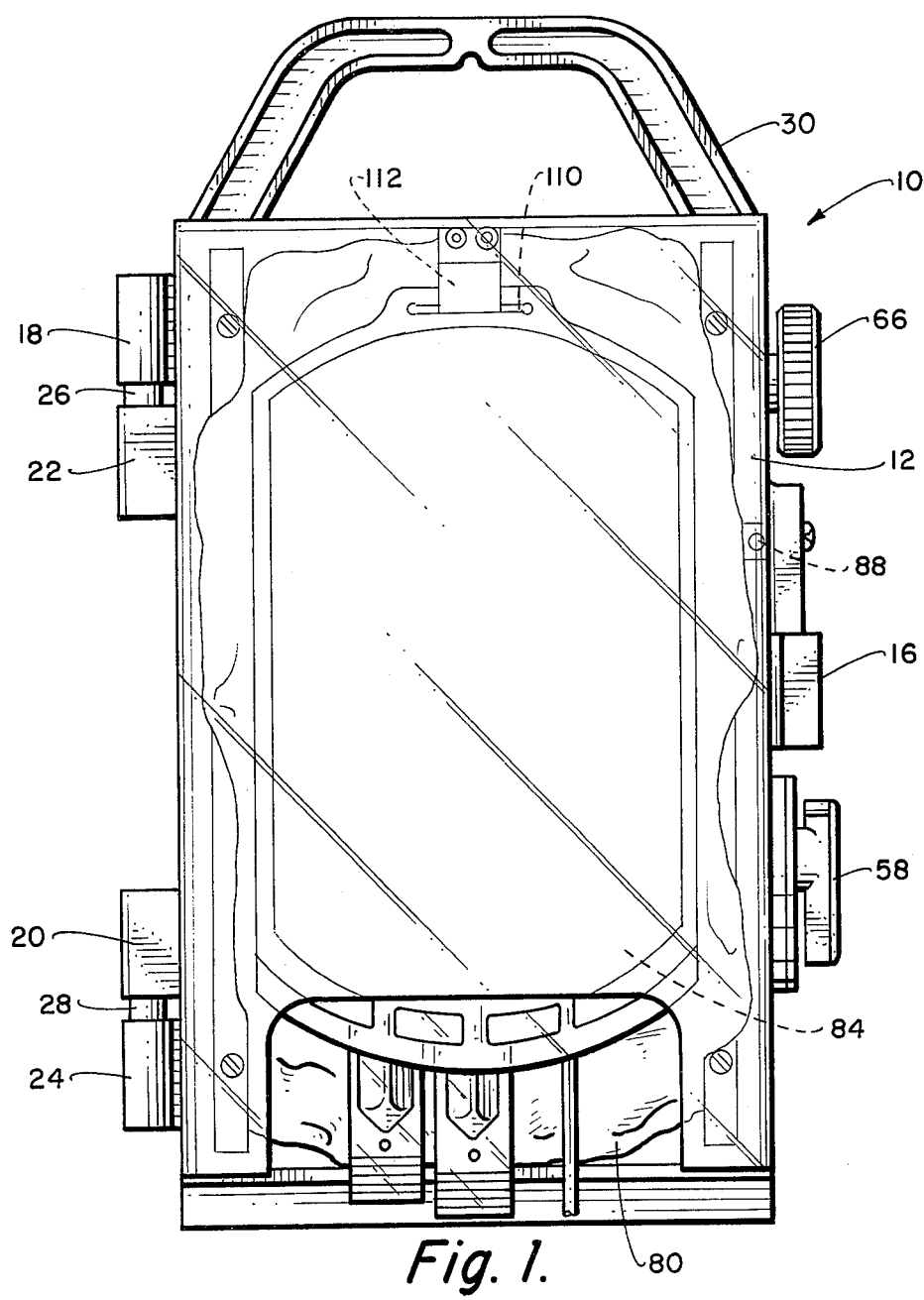
FIG. 1 is a front, elevational view of the blood pump of this invention.

Referring particularly to the drawing, there is shown the blood pump 10 of this invention which is composed generally of an access door 12 and a housing 14. The housing 14 is to be constructed of sheet material, such as plastic or metal, and is divided internally into a series of chambers 17, 19, and 21. Appropriate walls are located between the chambers 17, 19 and 21 in order to form the separate chambers.

The door 12 is to be formed of a transparent material, such as a clear plastic. One side of the door 12 includes a raised section which is to be engagable by the latching pawl 16. The latching pawl 16 is mounted on the exterior surface of the housing 14. The other side of the door 12 has fixedly mounted thereto a pair of spaced apart brackets 18 and 20. Both brackets 18 and 20 include an interior opening (not shown). Fixedly attached to an exterior surface of the housing 14 are brackets 22 and 24. Each of the brackets 22 and 24 include, respectively an upstanding pin. The pin 26 is to be located within the opening provided within the bracket 18 with the pin 28 to be located within the opening provided within the bracket 20. The net result is that a hinging movement is provided for the door 12 in respect to the housing 14.

It is to be understood that the pump 10 of this invention is to be readily portable and is to be a completely self-contained, operable unit. In order to facilitate portability, a handle 30 is attached to the exterior of the housing 14.

Figure 3:
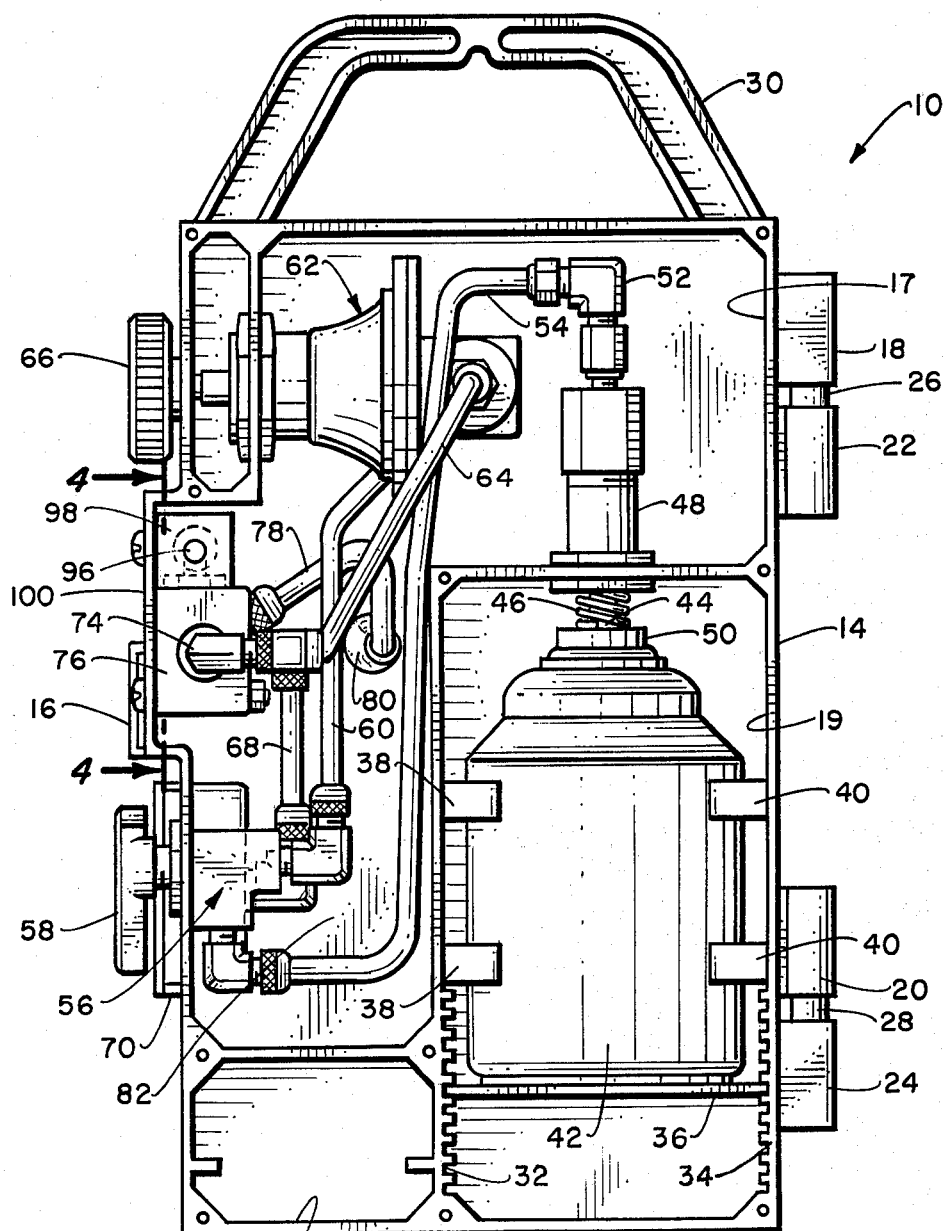
FIG. 3 is a cross-sectional view taken along line 3—3 of FIG. 2 of the blood pump of this invention.
Figure 6:
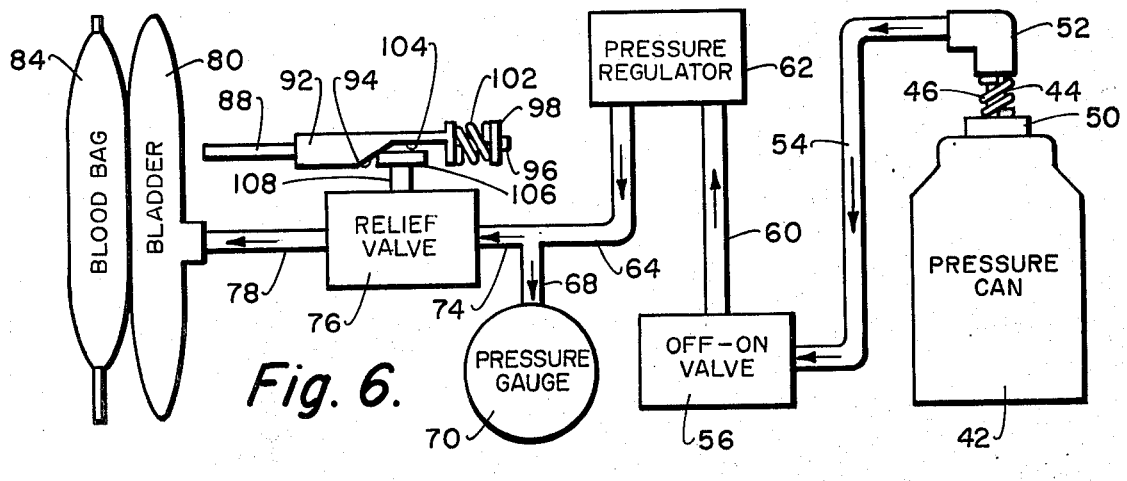
FIG. 6 is a schematic view depicting the operation of the blood pump of this invention.

Formed within a pair of spacing sidewalls of the chamber 19 are a series of grooves 32 and 34. The function of the grooves 32 and 34 are so that a single base plate can be connected between an aligned pair of grooves within the series of grooves 32 and 34. Such a locating of the base plate 36 is clearly shown in FIG. 3 of the drawing. It is to be noted that the base plate 36 can be moved to connect with any aligned pair of grooves within the series of grooves 32 and 34.

Fixedly attached to one of the sidewalls of the chamber 19 and adjacent the grooves 32 are a pair of spaced-apart cradle arms 38. A similar pair of cradle arms 40 are fixedly secured to the facing sidewall adjacent the series of grooves 34. The arms 38 and 40 function together to closely hold a container 42.

The container 42 is deemed to be replaceable. The container 42 is to contain a quantity of pressurized gas which could either comprise air, nitrogen, freon, etc. The base of the container 42 rests on the base plate 36. The structure of the container 42 is deemed to be conventional. The adjustability provided by the base plate 36 in respect to the grooves 32 and 34 is so that different heights of containers 42 could be utilized. Therefore, the pump 10 of the present invention is not be be limited to a specific manufactured height of container 42.

The upper end of the container 42 has an outlet valve in the form of a depressible stem (not shown). This stem is to be pressed by means of a plunger 44 about which is located a coil spring 46. The plunger 44 is movable within a gas fitting 48. The movement of the plunger 44 within the fitting 48 is accomplished in a manner to prevent leakage of gas from the fitting 48. The outer end of the plunger 44 is fixedly secured to a disc 50. There is located within the container 42 and about the outlet valve thereof an annular recess (not shown). The disc 50 is to fit within the annular recess in a tight fitting manner to prevent leakage of gas therebetween. The coil spring 46 functions to maintain a secure engagement between the disc 50 and the annular recess of the container 42. Also, in the locating of the container 42 in position, the coil spring 46 should be somewhat compressed prior to the inserting of the base plate 36 in its proper position located against the bottom surface of the container 42.

The pressurized gas is to be conducted through the fitting 48, through elbow fitting 52, and into conduit 54. The gas is conducted through conduit 54 into an on-off valve assembly 56. It is to be understood that plunger 44, coil spring 46, fitting 48 and conduit 54 are to be considered as part of valve assembly 56. Manual control of the on-off valve assembly 56 is provided through the use of knob 58. Knob 58 protrudes exteriorly of the housing 14 and is to be capable of being manually moved to either the off or on position. In the on position, pressurized gas is conducted through the valve assembly 56 into conduit 60. The gas within conduit 60 is conducted into a regulator assembly 62. The regulator 62 is deemed to be conventional and will normally take the form of a regular diaphragm type of gas regulator. The regulator 62 is located within the chamber 17. The pressurized gas, after being conducted through the regulator 62 is to be passed within conduit 64. The function of the regulator 62 is vary the pressure of the gas within the conduit 64. This variance is to be caused by manual rotating of the knob 66 which protrudes exteriorly of the housing 14. The gas under pressure within the conduit 64 is conducted into a conduit 68 to a pressure reading gauge 70. The gauge 70 is deemed to be conventional and includes a pointer 72 which is to be movable across appropriate indicia across the face of the gauge 70 in order to represent different pressure levels of the gas within the conduit 68. Turning of the knob 66 causes the pointer 72 to move across the face of the gauge 70. It is to be understood that the pressure gauge 70 is mounted within the housing 14 with the gauge 70 to be readily observable exteriorly thereof.

A connecting conduit 74 connects at the junction of the conduit 64 and 68 and in turn connects with a pressure relief valve assembly 76. The pressurized gas is to be conducted through the valve 76 and into a discharge conduit 78. Discharge conduit 78 connects with a bladder 80. The bladder 80 is located against forward wall 82 of the housing 14. The opposite side of the bladder 80 is to be located against blood bag 84 which is located within a storage chamber 86. The storage chamber 86 is located between the forward wall 82 and the interior of the door 12.

When the door 12 is closed, an edge of the door 12 contacts rod 88. Rod 88 is slidably movable within opening 90 formed within the forward wall 82. Rod 88 is fixedly attached to an enlarged section 92 which in turn has an inclined cam surface 94. The outer end of the enlarged section 92 is attached to rod 96. The rod 96 is slidably mounted within plate 98 which is fixedly mounted onto exterior plate 100. The plate 100 is fixedly attached to the housing 14 in the area between the knob 66 and the pressure gauge 70.

Figures 2, 5:
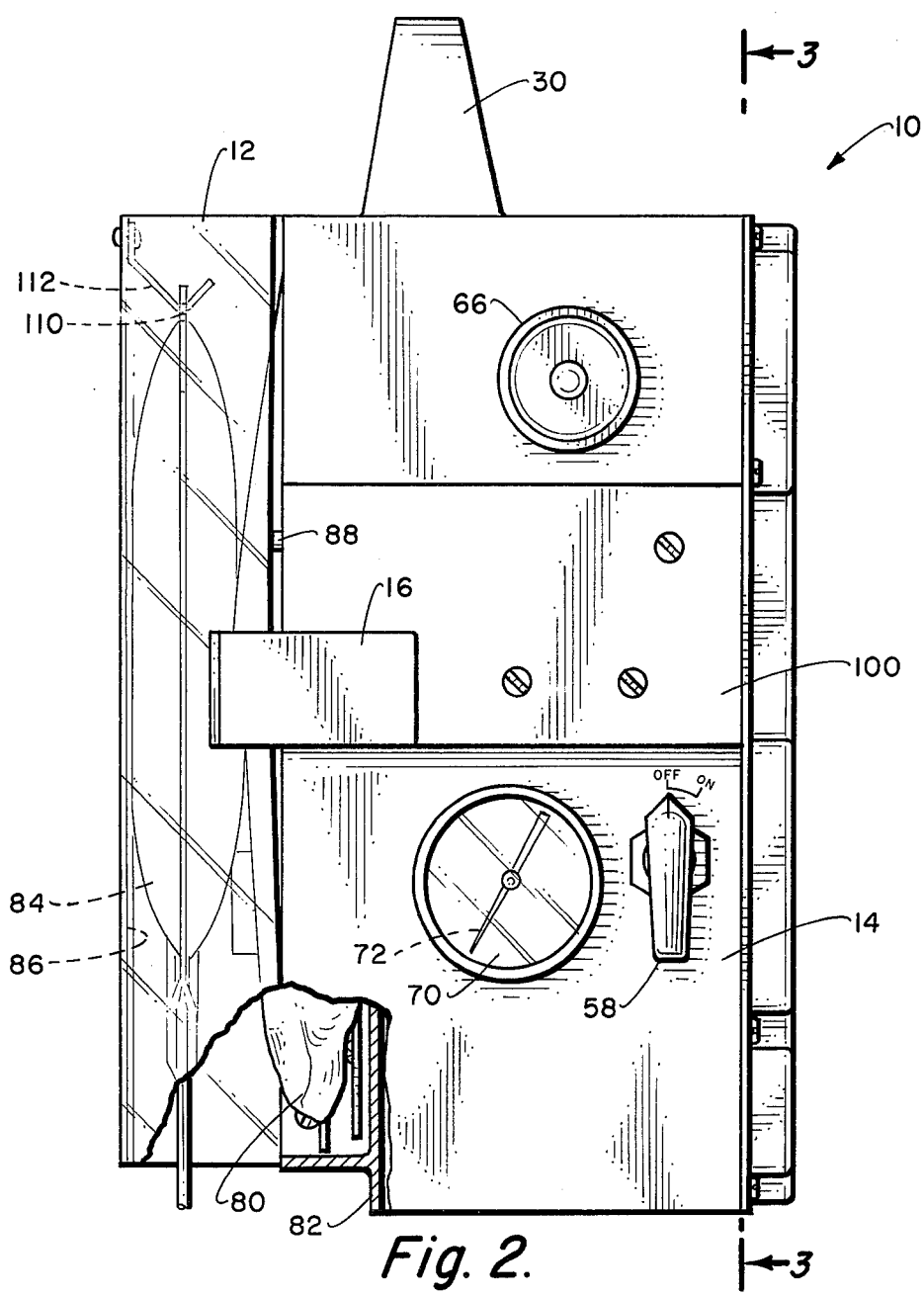
FIG. 2 is a right side elevational view of the blood pump of this invention.
FIG. 5 is a view similar to FIG. 4, but showing the door in the open position.

Located about the rod 96 and in between the enlarged section 92 and the plate 98 is a coil spring 102. The function of the coil spring 102 is to exert a continuous bias against the rod 88 tending to locate such in the position shown in FIG. 5.

Figure 4:
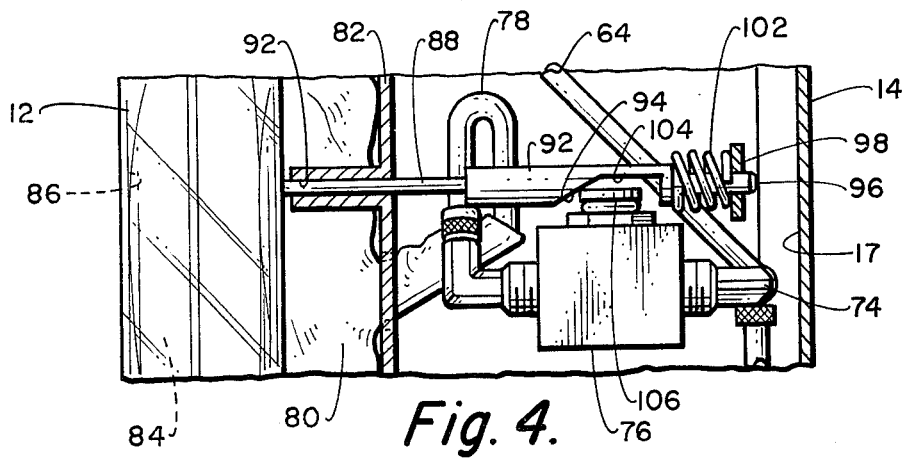
FIG. 4 is a segmental, cross-sectional view through a portion of the blood pump of this invention taken along line 4—4 of FIG. 3 showing the door in the closed position.

Formed within the section 92 is a cavity 104. The cavity 104 is to connect with head 106 of a valve spool 108. With the door 12 shut, as shown within FIG. 4, the rod 88 is located in the position so that the inclined surface 94 is in contact with the head 106 and causes the valve spool 108 to be moved downward to within the pressure relief valve assembly 76. It is to be understood that the spool 108 includes appropriate openings (not shown) which are located within the relief valve assembly 76. It is these openings that permit the gas to then be conducted through the valve spool 108 and into the conduits 78 and hence into the bladder 80. However, upon opening of the door 12, the rod 88 is moved to an extended position, as shown within FIG. 5, which causes the cam surface 94 to be moved out of engagement with the head 106. This results in the head 106 being located within the cavity 104. In this position, the solid structure of the valve spool 108 functions to form a blockage and prevent the conducting of gas from the conduit 74 into the conduit 78. At the same time, the conduit 78 is vented into the ambient out past the valve spool 108 and the head 106. As a result, the bladder 80 is deflated.

The operation of the blood pump of this invention is as follows. A pressurized container 42 is first inserted within the chamber 19 and is held in place by means of the base plate 36. At this particular time, pressurized gas from the container 42 is conducted through conduit 54 to the on-off valve assembly 56. The operator then opens the door 12 by disengaging the door with the latching pawl 16. The latching pawl 16 can be readily manually moved to a disconnected position with respect to the door 12. The operator then obtains a blood bag 84 which has a slot 110 formed in the upper end thereof. The slot 110 is then engaged with bracket 112 which is fixedly secured to the inside surface of the door 12. It is assumed that the blood bag 84 is filled with blood.

The operator then closes the door 12 engaging the door 12 with latching pawl 16. The operator then turns handle 58 from the off position shown in FIG. 2 to the on position. This causes pressurized gas to be conducted through the on-off valve assembly 56 through the regulator 62, through the pressure relief valve 76 and into the bladder 80. The bladder 80 is then inflated which presses against the blood bag 84. As to the amount of pressure being applied to squeeze the blood bag 84, this can be preset by the operator to a desired level by means of turning knob 66 of the regulator 62. By reading the position of the pointer 72 with respect to the face of the pressure gauge 70, the desired pressure being applied to the blood bag 84 can then be determined. This preset pressure level will be constantly maintained and as the blood within the blood bag 84 is decreased, the regulator 66 will automatically resupply additional pressurized gas into the bladder 80 so as to further expand the bladder 80 toward the blood bag 84 to therefore maintain the constant pressure being applied against the blood bag 84.

When the blood bag 84 is empty, the operator will only need to open the door 12 and to replace the empty blood bag 84 with a filled blood bag. Upon the door 12 being opened, the plunger 108 is moved to the upper position thereby preventing further gas supply into the bladder 80 and also venting the bladder 80 to the atmosphere. Upon reclosing of the door 12, the plunger 108 is moved to the downward position, which in turn causes pressurized gas to again be resupplied to the bladder 80.

Chamber 21 is provided to possibly include an electrical heater apparatus. The heater is to provide heat energy to the blood bag 84 so as to warm the blood prior to being infused into the patient. The addition of a heater is deemed to be optional.

What is claimed is:

1. In combination with a blood bag, a blood infusion pump comprising:
   a housing, said housing including a storage chamber for locating said blood bag;
   pressure applying means for applying an evenly distributed force to said blood bag; and
   pressure supply means for supplying a pressurized fluid through a conduit assembly to said pressure applying means, said pressure supply means comprising a container containing a quantity of pressurized fluid, said container being removable and replaceable within said housing, a valve assembly connected to said conduit assembly, said valve assembly to connect with said container to thereby supply the pressurized fluid from said container into said conduit assembly, said valve assembly being continuously spring biased into an airtight relationship with said container, said valve assembly being movable a limited amount in respect to said conduit assembly so as to positively engage in said airtight relationship with said container, whereby said pressurized fluid is conducted to said pressure applying means which causes blood to be discharged from said blood bag.

2. The combination as defined in claim 1 wherein:
   said housing including a door, said door being openable to permit access into said storage chamber, latching means mounted on said housing, said latching means for maintaining said door in the closed position.

3. The combination as defined in claim 1 including:
   a pressure regulator, said pressure regulator to be manually setable to different fluid pressure levels, whereby the greater the fluid pressure level also the greater the flow of blood through said discharge conduit assembly.

4. The combination as defined in claim 2 wherein:
   a pressure release valve located within said discharge conduit assembly, said pressure release valve to release fluid pressure from said pressure applying means when said access door is opened.

5. The combination as defined in claim 1 wherein:
   said pressure applying means taking the form of an inflatable bladder.

6. In combination with a blood bag, a blood infusion pump comprising:
   a housing, said housing including a storage chamber for locating said blood bag;
   pressure applying means for applying an evenly distributed force to said blood bag;
   pressure supply means for supplying a pressurized fluid through a conduit assembly to said pressure applying means, whereby said pressurized fluid is conducted to said pressure applying means which causes blood to be discharged from said blood bag;
   said housing including a door, said door being openable to permit access into said storage chamber, latching means mounted on said housing, said latching means for maintaining said door in the closed position;
   a pressure release valve located within said conduit assembly, said pressure release valve to release fluid pressure from said pressure applying means when said access door is opened;
   said pressure supply means comprising a container containing a quantity of pressurized fluid, a valve assembly connected to said conduit assembly, said valve assembly to connect with said container to thereby supply the pressurized fluid from said container into said conduit assembly;
   said valve assembly being continuously spring biased into an airtight relationship with said container, said valve assembly being movable a limited amount in respect to said conduit assembly; and
   said container being mounted on a container support assembly, said container support assembly being adjustable to accommodate different heights of containers.

7. The combination as defined in claim 6 wherein said housing including a door, said door being openable to permit access into said storage chamber, latching means mounted on said housing, said latching means for maintaining said door in the closed position.

8. The combination as defined in claim 7 wherein:
   a pressure release valve located within said discharge conduit assembly, said pressure release valve to release fluid pressure from said pressure applying means when said access door is opened.

9. The combination as defined in claim 8 wherein:
   said pressure applying means taking the form of an inflatable bladder.

\* \* \* \* \*